United States Patent
Bradley et al.

(12) 
(10) Patent No.: US 7,211,049 B2
(45) Date of Patent: May 1, 2007

(54) BREATH MEASUREMENT

(75) Inventors: Austen Peter Bradley, Manchester (GB); Paul Barraclough, Warrington (GB)

(73) Assignee: Nutren Technology Limited, Manchester (GB)

( * ) Notice: Subject to any disclaimer, the term of this patent is extended or adjusted under 35 U.S.C. 154(b) by 657 days.

(21) Appl. No.: 10/419,883

(22) Filed: Apr. 22, 2003

(65) Prior Publication Data
US 2004/0097820 A1    May 20, 2004

(30) Foreign Application Priority Data
Nov. 14, 2002  (GB) .................. 0226522.1

(51) Int. Cl.
*A61B 5/02* (2006.01)
(52) U.S. Cl. ...................................... 600/538
(58) Field of Classification Search ........... 600/529, 600/532; 73/23.2; 422/84
See application file for complete search history.

(56) References Cited

U.S. PATENT DOCUMENTS 6,454,724 B1 *  9/2002  Greene ........................ 600/534
6,502,572 B1 *  1/2003  Berthon-Jones et al. ..................... 128/204.23

* cited by examiner

*Primary Examiner*—Robert L. Nasser
(74) *Attorney, Agent, or Firm*—Squire, Sanders & Demsey L.L.P.

(57) ABSTRACT

The invention provides a breath monitoring device comprising means to record a first breathing state of a user, and means to detect a deviation from the recorded breathing state in a subsequent use of the device by a user. The invention further provides a method of monitoring breaths, the method comprising the steps of:
 (a) recording the first breathing state of a person from a breath of a person; and
 (b) detecting a deviation from the recorded first breathing state in a subsequent breath from a person.

35 Claims, 2 Drawing Sheets

BREATH MEASUREMENT

FIELD OF THE INVENTION

This invention relates to a breath monitoring apparatus and methods of monitoring breathing.

BACKGROUND TO THE INVENTION

It is known to provide instruments which measure a breathing parameter of a user's breath, and which displays the result of the measurement for a user, sports scientist or doctor to review, for example.

In particular, devices are known for use in calorimetry, to study the energy of metabolism in humans and animals. Calorimetry is used, for example, for diagnosis of metabolic disorders and for calculating nutritional requirements of a subject. A useful calorimetric measure for nutritional and sports scientists when assessing the health and fitness of a subject is the volume of oxygen consumed at rest, and during or after physical exertion.

Indirect calorimetry often involves measuring the amount of carbon dioxide exhaled by a subject, which can in turn be used to calculate the oxygen consumption of a subject.

The measurement of the volume of oxygen consumed and/or the amount of carbon dioxide exhaled by a subjected are normally measured as a single reading, at rest, during or after physical exertion. Multiple measurements may be taken and plotted on a chart to indicate changes in oxygen and/or carbon dioxide measured over a period of time.

One problem with measuring parameters of breathing states, such as volume of oxygen consumed at rest and/or during or after physical exertion, is that the devices used to monitor the breathing parameter lead the user to "force" a breath, due to having to exhale and inhale through a breathing tube attached to the device. Thus the subject does not always breathe normally, and forces a breath from their lungs, or into their lungs as an instinctive reaction. The measurement of forced breaths does not give an accurate indication of the breathing parameter measured, as the breath will generally have a greater volume, speed, oxygen and/or carbon dioxide content or, if multiple breaths are measured, have irregular time intervals between breaths, or a lower or higher number of breaths in a predetermined time period than would be measured during normal breathing. It would be advantageous to provide a breath monitoring device which allows a user to determine whether a monitored breathing state is a "normal" breath or a "forced" breath.

Furthermore, with known devices for monitoring breath parameters, it is not generally possible to determine whether or not, during subsequent use of the devices, whether the same user is breathing into the device during each monitoring session. Thus, it would be advantageous to provide a device which would monitor and determine whether or not the same user is using the monitoring device on subsequent uses, after detecting and storing breath parameters of a specified user.

It is therefore an aim of preferred objects of the present invention to overcome or mitigate at least one of the problems of the prior art, whether expressly described hereinabove or not.

SUMMARY OF THE INVENTION

According to a first aspect of the invention there is provided a breath monitoring device comprising means to record a first breathing state of a user, and means to detect a deviation from the recorded breathing state in a subsequent use of the device by a user.

Suitably the device comprises a housing in which the recording means and detection means are located.

Suitably the means to record a first breathing state of a user comprise means to record at least one breath parameter of a user. Preferred breath parameters which may be recorded include at least one parameter selected from inhalation speed, exhalation speed, inhalation volume, exhalation volume, oxygen content of exhaled breath, carbon dioxide content of exhaled breath, time interval between breaths, number of breaths in a predetermined time period, duration of an exhalation, duration of an inhalation and the rate of change of any of the aforementioned parameters.

Thus, suitable means to record a first breathing state of a user may be one or more means selected from an inhalation speed sensor, an exhalation speed sensor, an inhalation volume sensor, an exhalation volume sensor, an inhalation duration sensor, an exhalation duration sensor, an inhalation pressure sensor and an exhalation pressure sensor.

Suitably the means to record a first breathing state of a user comprise means to record an unforced breathing state. By "unforced" we mean the user breathes naturally without blowing, sucking, exhaling the lungs' void space volume, or otherwise actively altering the speed and/or volume of inhaled and/or exhaled breath whether consciously or subconsciously. Thus an "unforced" breathing state may be a resting breathing state or the breathing state of the user after physical activity or exertion.

The means to detect a deviation from the first breathing state preferably comprise the means to record the first breathing state.

Suitably the means to detect a deviation from the first breathing state comprise means to detect when a user other than the first user uses the device.

Preferably the device further comprises means to store data obtained from the first breathing state recordal means.

Suitably the data storage means comprises a machine readable medium, on which data may be stored by any suitable means, such as optically, magnetically, chemically, or electrically, or any combination thereof for example.

Suitably the data storage means comprises a computer hard disk, chip-based memory (such as RAM or EPROM for example), floppy disk, compact disc, DVD (digital versatile disc), mini-disc or the like. While the above mentioned data storage means are all digital the data storage means may comprise analogue data storage means.

Thus, the device may record the first breathing state of the first user, which is then stored in the data storage means. If, subsequently a second user then uses the device, the parameter(s) of the second user's breathing will be recorded by the recording means and compared to the stored data in the data storage means, by the means to detect a deviation from the first breaking state. The deviation detection means will then determine that a deviation has taken place and indicate the deviation accordingly.

Suitably the device further comprises indicator means, arranged to indicate when a deviation from the first breathing state is detected by the deviation detection means.

The indicator means, may be visual indicator means, audio indicator means, or both visual and audio indicator means.

Suitable visual indicator means include light emitting diodes, liquid crystal display panels, warning lights or lamps, visual text displays and the like, for example. In preferred embodiments the visual indicator means comprise means to display text. Suitably the indicator means is capable of displaying the extent of the deviation of the or each breath parameter which does not conform to the or each breath parameter of the first breathing state.

Suitable audio indicator means include warning buzzers, bells, sirens or the like, and vocal warnings, for example.

The device may comprise means to temporarily prevent operation of the device by a user, when a deviation from the first breathing state is detected. The device operation prevention means may prevent operation for a defined time period, which may be set by a user, or may prevent operation until a user manually overrides the operation prevention means, such as by way of a manual switch or other similar means, for example.

The device operation prevention means may comprise a switch or trigger, for example which is activated when the deviation detection means detects a deviation from the first breathing state. The device operation prevention means, may prevent subsequent breaths by a user from entering the device, or may prevent recordal of subsequent breaths by the recordal means, for example.

The device may further comprise means for a user to accept or decline a breath recordal, whether the breath is within the parameters of the first breathing state or is a deviation from the first breathing state. The breath recordal acceptance means may comprise a switch, or similar member, which in use must be activated to accept a breath reading in order for the reading to be recorded by the means to record the first breathing state of a user.

Preferably the device comprises a fluid inlet, which in use is arranged to allow passage of a user's breath into and out of the device.

Preferably the fluid inlet comprises a mouthpiece, integral with or connected to the fluid inlet. Suitably the mouthpiece is detachably connected to the fluid inlet, which enables the mouthpiece to be cleaned between uses.

The mouthpiece preferably comprises a mask arranged in use to be placed over at least the mouth of a user, and more preferably the mouth and nose of a user. Suitably the mask has securement means, arranged to secure the mask to a user's face. A mask is preferred as a mouthpiece as it encourages normal, unforced breathing from a user. Other mouthpieces, such as tubes, which are arranged to partially enter a user's mouth, may tend to encourage a user to force breaths into and/or out of a fluid inlet.

According to a second aspect of the present invention there is provided a method of monitoring breaths, the method comprising the steps of:

(a) recording a first breathing state of a person from a breath of a person; and (b) detecting a deviation from the recorded first breathing state in a subsequent breath from a person.

Step (a) may comprise recording a first breathing state determined from a plurality of breaths from the person.

Step (a) may comprise monitoring at least one breath parameter of the person's breath. Preferred breath parameters include at least one parameter selected from inhalation speed, exhalation speed, inhalation volume, exhalation volume, oxygen content of exhaled breath, carbon dioxide content of exhaled breath, time interval between breaths, number of breaths in a predetermined time period, duration of an exhalation, duration of an inhalation and the rate of change of any of the aforementioned parameters.

Suitably step (b) comprises comparing one or more subsequent breaths of a person with the first breathing state recorded from the or each breath recorded in step (a).

Suitably there is a step between step (a) and (b) of storing data obtained from the recordal of the first breathing state of the person in step (a). Suitably step (b) comprises detecting a deviation from the stored data.

Step (b) may comprise detecting a deviation from a subsequent breath or breaths originating from the same person as step (a), or from a different person. Thus the method may comprise distinguishing between a first breathing state of a first person, and a breathing state of a second person.

Suitably the method comprises a step (c) of indicating when a deviation has been detected. Suitably the indication may be a visual and/or audio indication.

According to a third aspect of the invention there is provided the method of monitoring breaths of the second aspect of the invention, using a breath monitoring device of the first aspect of the invention.

BRIEF DESCRIPTION OF THE DRAWINGS

For a better understanding of the invention, and to show how embodiments of the same may be put into effect, the various aspects of the invention will now be described by way of example with reference to the accompanying drawings, in which.

DESCRIPTION OF THE PREFERRED EMBODIMENT

Figure 1A:
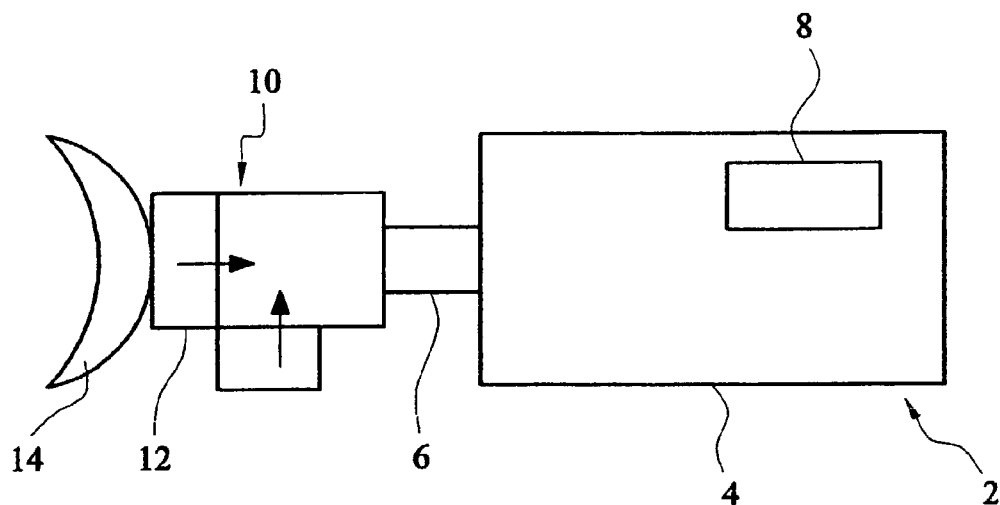
FIG. 1A illustrates a side elevation of a preferred embodiment of a breath monitoring device of the invention, including a face mask for recording the first breathing state of a user.
Figure 1B:
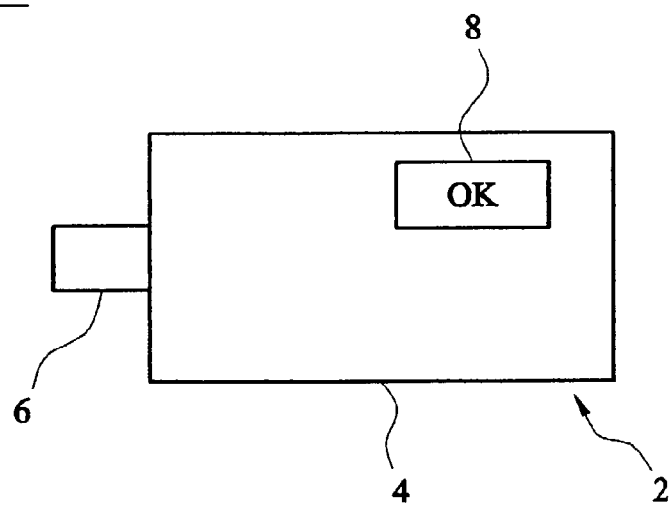
FIG. 1B illustrates the breath monitoring device of FIG. 1A during use, when a deviation from the first breathing state has been detected.
Figure 1C:
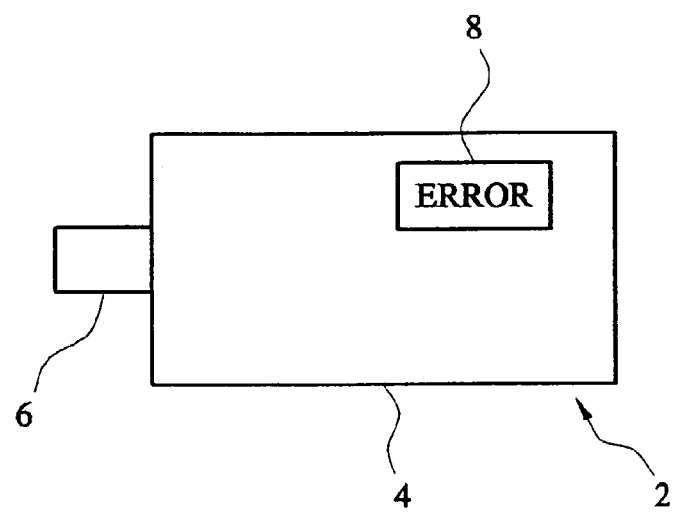
FIG. 1C illustrates the breath monitoring device of FIG. 1A during use when a deviation has not been detected.

We refer firstly to FIGS. 1A to 1C. A preferred embodiment of a breath monitoring device 2 of the invention comprises a housing 4 in which is housed a means to record a first breathing state of a user, in the form of a combined exhalation speed and volume monitor (not shown), a data storage means in the form of a memory chip consisting of RAM or EPROM, and a means to detect a deviation from the first breathing state which comprises the means to record the first breathing state (and to record subsequent breaths). Thus the means to record a first breathing state of a user and means to detect a deviation from the first breathing state comprise one and the same means in this preferred embodiment.

Breath exhalation speed and volume monitors are well known, and any suitable monitor may be used such as a Peak Flow Meter. The breath monitoring device also includes an indicator means in the form of a liquid crystal display panel 8, set into the housing 4, and operably connected to the recording means, deviation detection means and data storage means. Extending from one end of the housing 4, and also operably connected to the breath recordal means, data storage means and deviation detection means, is a fluid inlet 6. A detachable mouthpiece 10, as shown in FIG. 1A, can be connected to the fluid inlet 6. The mouthpiece 10 includes a T-valve 12, which allows exhaled breath to enter the fluid inlet 6 and into the device 2, but allows air from outside of the device 2 to be inhaled through the T-valve when a user inhales. The distal end of the T-valve includes a flexible mask 14 arranged in use to be connected over the mouth of a user.

Use of the device 2 will now be described with reference to FIGS. 1A to 1C, and FIGS. 2A to 2C.

A user firstly connects the detachable mouthpiece 10 to the fluid inlet 6 of the housing 4 of the device 2. When it is desired to record a first breathing state of the user, the user places the facemask 14 over his or her mouth, and begins to breathe into the mouthpiece 10. It is generally preferable to record a first breathing state in which the breathing state is unforced, that is the user breathes naturally into the mask 14 rather than forcing air into the mask and through the fluid inlet. The use of a mask 14 helps to produce unforced breathing by a user. If the mask 14 is not present, a user may tend to force exhalations into the fluid inlet 6.

As a user breaths into the mask 14, exhaled breath enters the fluid inlet 6 through the T-valve 12, and into the housing 4 of the device, where the desired parameters of the first breathing state are recorded, such as exhalation speed, and exhalation volume. When the user inhales, air is drawn through the T-valve from outside of the device 4, and through the mask 14 into a user's lungs and/or airways. The user may continue to breathe into the device 2 for a prescribed period of time, until a first breathing state is recorded. The first breathing state may be recorded from just one breath or a plurality of breaths over a user-defined or device-defined period of time. When the first breathing state has been recorded satisfactorily, the liquid crystal display panel 8 will indicate to the user that the breathing state has been recorded. In alternative embodiments the indicator means may be lights and/or warning sounds.

Figure 2A:
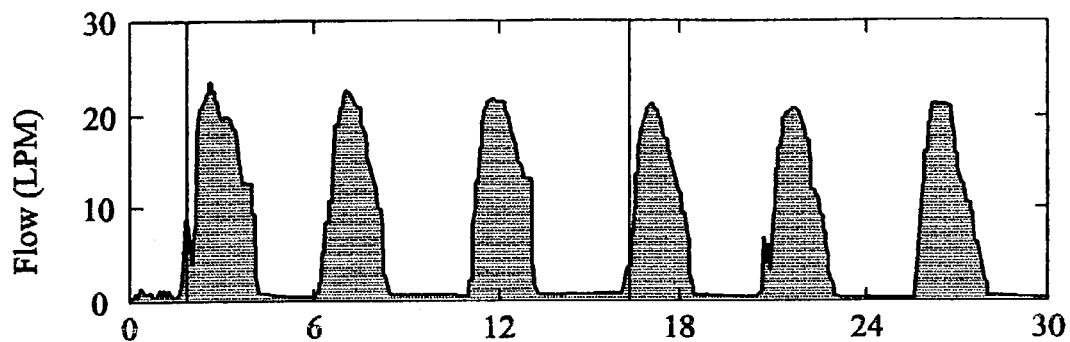
FIG. 2A is a graph showing the result of recordal of a first breathing state of a user using the breath monitoring device of FIG. 1A–1C.

FIG. 2A shows a graph of a recorded first breathing state of a user, in which the volume of exhaled air, and the duration of an exhaled breath have been monitored as the parameters of the first breathing state. In this example, the user exhaled for approximately 3 seconds per breath, with a flow of approximately 22 LPM (litres per minute). The recordal in this example was effected over a period of 30 seconds, such that a mean exhalation duration and flow could be recorded, and stored on the data storage means (not shown).

Figure 2B:
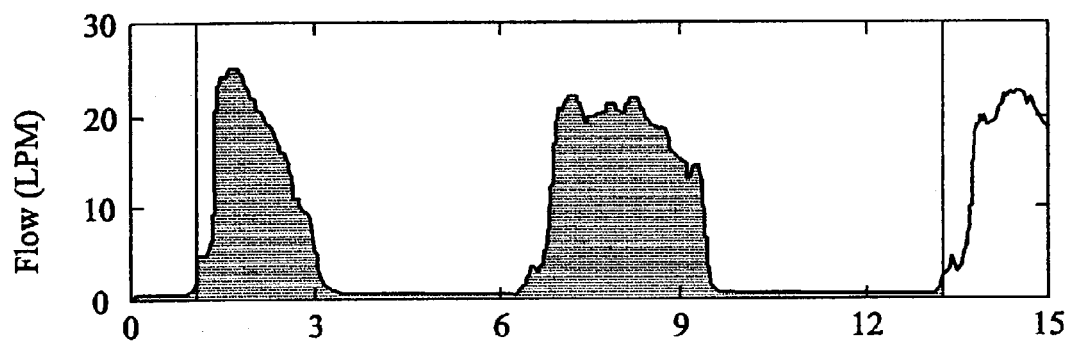
FIG. 2B is a graph showing deviation in a breath from the first breathing state of a first user, in a subsequent use of the breath monitoring device of FIGS. 1A–1C by the same user.

Once the first breathing state has been monitored and stored on the data storage means, the mouthpiece 10 may be optionally removed, as shown in FIGS. 1B and 1C. When it is desired for the first user to have his or her breath monitored again, the user may place his or her mouth on the fluid inlet (or mouthpiece 10), and breathe into the device 2. As a first user exhales into the device, the means to detect deviation from the first breathing parameter will monitor the user's breathing, and detect if any deviation from the first recorded breathing state has occurred. FIG. 2B shows a subsequent use of the device 2 by the first user of the recorded breathing state of FIG. 2A, in which the first breath, between 1 and 3 seconds, had been recorded and monitored by the deviation detection means, as corresponding within the parameters of the first breathing state of FIG. 2A (in that the duration of exhalation and the flow were within acceptable deviation from the first breathing state recorded in FIG. 2A). Thus for the first exhaled breath, the liquid crystal display means 8 signals that the breath is within the first breathing state recorded on the data storage means and records an "ok" display, as shown in FIG. 1B. If a user forces breath into the device 2 into the fluid inlet 6, as shown in the second breath on the graph of FIG. 2B, the deviation monitoring means will record that the exhalation has an increased duration, and, as shown in FIG. 1C will indicate on the liquid crystal display 8 that a breath falling outside of the first breathing state has occurred.

Figure 2C:
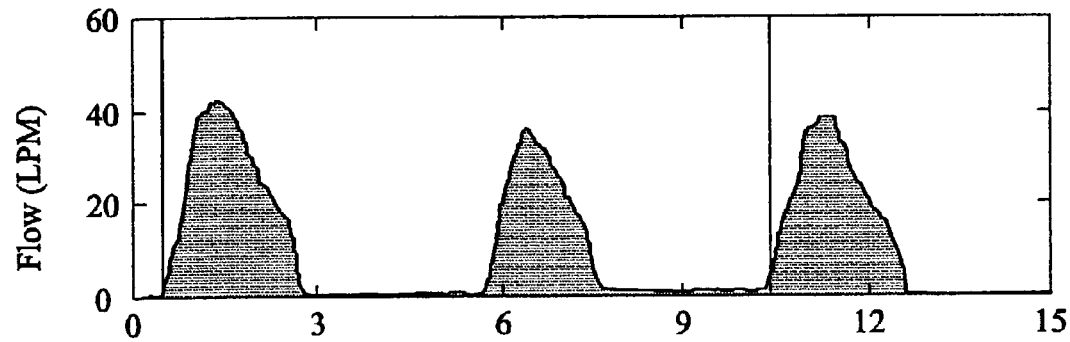
FIG. 2C is a graph showing deviations from the first breathing state of the first user, in a subsequent use of the breath monitoring device of FIGS. 1A to 1C by a second user.

FIG. 2C shows recordal of breaths from a second, different user to the first user of the device 2. When the second user breathes into the device 2, the duration of exhalation, as shown in FIG. 2C, is longer than the duration of exhalation of the first user, and the flow is substantially higher (approximately 40 LPM). The deviation detection means detects that a second user is using the device 2, and displays an error message as shown in FIG. 1C. Thus the device can be tailored to suit an individual, and prevent use of the device when a second user subsequently uses it.

The device 2 may be used to monitor a first breathing state of a user when the user is at rest, or after physical exercise. The device 2 is particularly useful for when a user has undergone physical exercise, as there is a tendency for users to breathe into breath monitoring devices in a forced state, which does not accurately represent the volume, duration and gas content of the unforced breaths.

The device 2 may form part of a direct or indirect calorimeter, which measures metabolism by monitoring oxygen or carbon dioxide volume in exhaled and inhaled gas. Thus use of the device will prevent a user from forcing excess air into the calorimeter, thereby adversely affecting the results on metabolism study.

In alternative embodiments of the breath monitoring device of the invention, there may be a means for the device to prevent a user from operating the device after a deviation from the first breathing state has been detected and/or indicated in subsequent breaths from a user. The operation prevention means may comprise a switch which, when the deviation detection means detects a deviation from the first breathing state, is triggered to prevent exhaled breath entering the device through the mouthpiece, for example.

The device may also comprise means for a user to manually override the operation prevention means, such as a manual switch connected thereto, for example.

There may also be a means on the device for a user to accept or decline a breath reading by the means to record a first breathing state (whether accepted by the device as within the first breathing state parameter or not). The breath reading acceptance means may comprise a switch or other similar member which must be activated in order for the first breathing state recordal means to record a breath reading.

The reader's attention is directed to all papers and documents which are filed concurrently with or previous to this specification in connection with this application and which are open to public inspection with this specification, and the contents of all such papers and documents are incorporated herein by reference.

All of the features disclosed in this specification (including any accompanying claims, abstract and drawings), and/or all of the steps of any method or process so disclosed, may be combined in any combination, except combinations where at least some of such features and/or steps are mutually exclusive.

Each feature disclosed in this specification (including any accompanying claims, abstract and drawings), may be replaced by alternative features serving the same, equivalent or similar purpose, unless expressly stated otherwise. Thus, unless expressly stated otherwise, each feature disclosed is one example only of a generic series of equivalent or similar features.

The invention is not restricted to the details of the foregoing embodiment(s). The invention extend to any novel one, or any novel combination, of the features disclosed in this specification (including any accompanying claims, abstract and drawings), or to any novel one, or any novel combination, of the steps of any method or process so disclosed.

The invention claimed is:

1. A breath monitoring device comprising:
   means to record a first breathing state of a user;
   means to detect a deviation from the recorded breathing state in a subsequent use of the device by a user; and
   means for accepting or declining a breath recordal by a user, whether a breath is within the parameters of the first breathing state or is a deviation from the first breathing state.

2. A breath monitoring device as claimed in claim 1 comprising a housing in which the recording means and detection means are located.

3. A breath monitoring device as claimed in claim 1 wherein the means to record a first breathing state of the user comprises means to record at least one breath parameter of a user.

4. A breath monitoring device as claimed in claim 3 wherein the at least one breath parameter comprises at least one of inhalation speed, exhalation speed, inhalation volume, exhalation volume, oxygen content of exhaled breath, carbon dioxide content of exhaled breath, time interval between breaths, number of breaths in a predetermined time period, duration of an exhalation, duration of an inhalation, and the rate of change of any of the aforementioned parameters.

5. A breath monitoring device as claimed in claim 1 wherein the means to record a first breathing state of a user is one or more means selected from an inhalation speed sensor, an exhalation speed sensor, an inhalation volume sensor, an exhalation volume sensor, an inhalation duration sensor, an exhalation duration sensor, an inhalation pressure sensor and an exhalation pressure sensor.

6. A breath monitoring device as claimed in claim 1 wherein the means to record a first breathing state of a user comprises means to record an unforced breathing state.

7. A breath monitoring device as claimed in claim 6, wherein the unforced breathing state is a resting breathing state or the breathing state of the user after physical activity or exertion.

8. A breath monitoring device as claimed in claim 1, wherein the means to detect a deviation from the first breathing state preferably comprises the means to record the first breathing state.

9. A breath monitoring device as claimed in claim 1, wherein the means to detect a deviation from the first breathing state comprises means to detect when a user other than the first user uses the device.

10. A breath monitoring device as claimed in claim 1, wherein the device further comprises means to store data obtained from the first breathing state recordal means.

11. A breath monitoring device as claimed in claim 1, wherein the data storage means comprises a machine readable medium, on which data may be stored by any suitable means.

12. A breath monitoring device as claimed in claim 11, wherein the data storage means comprises a computer hard disk, chip-based memory, floppy disk, compact disc, DVD (digital versatile disc), or mini-disc.

13. A breath monitoring device as claimed in claim 1, wherein the device further comprises indicating means, arranged to indicate when a deviation from the first breathing state is detected by the deviation detection means.

14. A breath monitoring device as claimed in claim 13, wherein the indicating means is a visual indicating means, audio indicator means, or both visual and audio indicator means.

15. A breath monitoring device as claimed in claim 14, wherein the indicating means is capable of displaying the extent of the deviation of the or each breath parameter which does not conform to the or each breath parameter of the first breathing state.

16. A breath monitoring device as claimed in claim 1, comprising means to temporarily prevent operation of the device by a user, when a deviation from the first breathing state is detected.

17. A breath monitoring device as claimed in claim 16, wherein the device operation prevention means prevents operation for a defined time period.

18. A breath monitoring device as claimed in claim 16, wherein the device operation prevention means comprises a switch or trigger which is activated when the deviation detection means detects a deviation from the first breathing state.

19. A breath monitoring device as claimed in claim 16, wherein the device operation prevention means prevents subsequent breaths by a user from entering the device, or prevents recordal of subsequent breaths by the recordal means.

20. A breath monitoring device as claimed in claim 1, wherein the means for accepting or declining a breath recordal comprises a switch which in use must be activated to accept a breath reading in order for the reading to be recorded by the means to record the first breathing state of a user.

21. A breath monitoring device as claimed in claim 1 comprising a fluid inlet, which in use is arranged to allow passage of a users breath into and out of the device.

22. A breath monitoring device as claimed in claim 21, wherein the fluid inlet comprises a mouthpiece.

23. A breath monitoring device as claimed in claim 22, wherein the mouthpiece is detachably connected to the fluid inlet.

24. A breath monitoring device as claimed in claim 22, wherein the mouthpiece comprises a mask configured to be placed over at least the mouth of a user.

25. A method of monitoring breaths, the method comprising the steps of:
   (a) recording the first breathing state of a person from a breath of a person;
   (b) detecting a deviation from the recorded first breathing state in a subsequent breath from a person; and
   (c) allowing a user to accept or decline a breath recordal, dependent on whether a breath is within parameters of the first breathing state or is a deviation from the first breathing state.

26. A method as claimed in claim 25, wherein step (a) comprises recording a first breathing state determined from a plurality of breaths from the person.

27. A method as claimed in claim 25, wherein step (a) comprises monitoring at least one breath parameter of the persons breath.

28. A method as claimed in claim 27, wherein the at least one breath parameter comprises at least one of inhalation speed, exhalation speed, inhalation volume, exhalation volume, oxygen content of exhaled breath, carbon dioxide content of exhaled breath, time interval between breaths, number of breaths in a predetermined time period, duration of an exhalation, duration of an inhalation, and the rate of change of any of the aforementioned parameters.

29. A method as claimed in claim 25, wherein step (b) comprises comparing one or more subsequent breaths of a person with the first breathing state recorded from the or each breath recorded in step (a).

30. A method as claimed in claim 25, wherein there is a step between step (a) and (b) of storing data obtained from the recordal of the first breathing state of the person in step (a).

31. A method as claimed in claim 25, wherein step (b) comprises detected a deviation from the stored data.

32. A method as claimed in claim 25, wherein step (b) may comprise detecting a deviation from a subsequent breath or breaths originating from the same person as step (a), or from a different person.

33. A method as claimed in claim 32, wherein the method comprises distinguishing between a first breathing state of a first person and a breathing state of a second person.

34. A method as claimed in claim 25 comprising a step (c) of indicating when a deviation has been detected.

35. A method of monitoring breaths as claimed in claim 25, further comprising a step of providing a breath monitoring device comprising means to record a first breathing state of a user, and means to detect a deviation from the recorded breathing state in a subsequent use of the device by a user.

* * * * *